United States Patent [19]

Hill

[11] 4,096,250

[45] Jun. 20, 1978

[54] TRI-SUBSTITUTED PHOSPHINEGOLD(I) 1-THIO-β-D-GLUCOPYRANOSIDES

[75] Inventor: David T. Hill, North Wales, Pa.

[73] Assignee: SmithKline Corporation, Philadelphia, Pa.

[21] Appl. No.: 772,035

[22] Filed: Feb. 25, 1977

[51] Int. Cl.² .................... A61K 31/70; C07H 11/04; C07H 13/12
[52] U.S. Cl. .................................. 424/180; 260/430; 536/118; 536/121; 536/122; 536/117
[58] Field of Search ............... 536/117, 118, 121, 122; 424/180

[56] References Cited

U.S. PATENT DOCUMENTS 3,635,945  1/1972  Nemeth et al. ...................... 536/121

*Primary Examiner*—Johnnie R. Brown
*Attorney, Agent, or Firm*—Joan S. Keps; Richard D. Foggio; William H. Edgerton

[57] ABSTRACT

The compounds are tri-substituted phosphinegold(I) 1-thio-β-D-glucopyranosides which have antiarthritic activity and, in particular, are of use in the treatment of rheumatoid arthritis. Of the three substituents on the phosphine one is optionally substituted phenyl and the others are lower alkyl or lower alkoxy.

7 Claims, No Drawings

TRI-SUBSTITUTED PHOSPHINEGOLD(I) 1-THIO-β-D-GLUCOPYRANOSIDES

This invention relates to new tri-substituted phosphinegold(I) 1-thio-β-D-glucopyranosides, one of the phosphine substituents being optionally substituted phenyl and the other two being lower alkyl or lower alkoxy. These compounds have antiarthritic activity and, in particular, are of use in the treatment of rheumatoid arthritis.

The compounds of this invention are represented by the following formula:

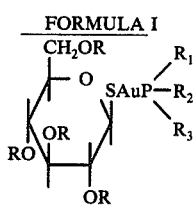

FORMULA I in which:
R is hydrogen, acetyl, lower alkyl-NHCO, lower alkyl-$SO_2$ or lower alkyl;
$R_1$ is phenyl optionally substituted by halogen or lower alkoxy and
$R_2$ and $R_3$ are lower alkyl or lower alkoxy.

Preferably, in Formula I, R is acetyl. Also, preferably, $R_2$ and $R_3$ are ethyl.

A preferred compound of this invention is represented by Formula I in which R is acetyl, $R_1$ is phenyl and $R_2$ and $R_3$ are ethyl, said compound being S-[(diethyl)(phenyl)phosphine]gold(I) 2,3,4,6-tetra-O-acetyl-1-thio-β-D-glucopyranoside.

The compounds of Formula I in which R is acetyl are prepared by reacting an S-(2,3,4,6-tetra-O-acetyl-β-D-glucopyranosyl)thiopseudourea hydrohalide with an aqueous solution of an alkali metal carbonate, preferably potassium carbonate, and reacting the resulting alkali metal salt of 2,3,4,6-tetra-O-acetyl-1-thio-β-D-glucopyranose with a halo(tri-substituted phosphine)-gold(I) compound of the formula:

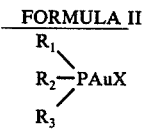

FORMULA II in which $R_1$, $R_2$ and $R_3$ are as defined above and X is a halide, preferably chloride.

The halo(tri-substituted phosphine)gold(I) compounds of Formula II may be prepared by reacting thiodiglycol with gold acid halide trihydrate to give halo[di(2-hydroxyethyl)sulfide]gold(I) which is then reacted with a tri-substituted phosphine.

The compounds of Formula I in which R is hydrogen are prepared by reacting a halo(tri-substituted phosphine)gold(I) compound of Formula II with an alkali metal salt of 1-thio-β-D-glucopyranose, preferably the sodium salt, to give the S-(tri-substituted phosphine)-gold(I) 1-thio-β-D-glucopyranosides. The reaction may be carried out in a nonreactive organic solvent at about −20° to −10° C. Alternatively, the reaction may be carried out in water at about 0° C.

The compounds of Formula I in which R is lower alkyl-NHCO are prepared by reacting the above prepared glucopyranosides in which R is hydrogen with a N-loweralkylcarbamoylating agent such as a lower alkyl isocyanate. The reaction may be conveniently carried out at room temperature using an excess of the lower alkyl isocyanate.

The compounds of Formula I in which R is loweralkyl-$SO_2$ are prepared by loweralkylsulfonylating a 1-(protected)thio-β-D-glucopyranose, for example using a loweralkylsulfonyl halide, removing the thio protecting group and treating with halo(tri-substituted phosphine)gold(I). For example, the protecting group on the 1-thio may be a trityl group which may be removed by treating with silver nitrate to give the silver salt of tetra-O-(loweralkylsulfonyl)-1-thio-β-D-glucopyranose which is then treated with halo(tri-substituted phosphine)gold(I).

The compounds of Formula I in which R is lower alkyl are prepared by O-loweralkylating D-glucose, then brominating the resulting 2,3,4,6-tetra-O-loweralkylglucose, reacting the resulting 1-bromo compound with thiourea, then by the procedures described above treating the 1-thiopseudourea with an alkali metal carbonate to give the alkali metal salt of 2,3,4,6-tetra-O-loweralkyl-1-thio-β-D-glucopyranose which is reacted with halo(tri-substituted phosphine)gold(I).

The compounds of Formula I are useful in treatment of arthritis. This activity is demonstrated by the following test procedures.

Inhibition of adjuvant induced polyarthritis in rats, as measured by reduction of rat paw edema, is produced by compounds of this invention at daily oral doses of about 20 mg./kg. (calculated on gold content). In this test procedure, adjuvant arthritis in rats is produced by a single intradermal injection of 0.75 of *Mycobacterium butyricum* suspended in white paraffin oil into the left hindpaw footpad. The injected paw becomes inflamed (increased volume) and reaches maximal size within three to five days (primary lesion). The animals exhibit a decrease in body weight gain during the initial period. The adjuvant arthritis (secondary lesion) occurs after approximately ten days and is characterized by inflammation of the non-injected right hind leg, decrease in body weight, and further increase in the volume of the injected left hind leg. Test compounds are administered daily, beginning on the day of the adjuvant injection, for 17 days thereafter, exclusive of days 4, 5, 11 and 12. Antiarthritic activity is shown by the ability to inhibit the development of either primary or secondary lesions of adjuvant arthritis.

The compounds of this invention are administered in conventional dosage forms prepared by combining a compound of Formula I in an amount sufficient to produce antiarthritic activity with standard pharmaceutical carriers according to conventional procedures. These procedures may involve mixing, granulating and compressing or dissolving the ingredients as appropriate to the desired preparation. The resulting pharmaceutical compositions are also objects of this invention. Oral dosage forms are preferred.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or nonaqueous liquid suspension.

Preferably, each dosage unit will contain the active ingredient in an amount of from about 1 mg. to about 10 mg.

The method of producing antiarthritic activity by administering internally to an animal a compound of Formula I is also an object of this invention. The compounds of Formula I are administered in an amount sufficient to produce antiarthritic activity. The route of administration may be orally or parenterally, preferably orally. Advantageously, doses will be administered 1 or 2 times a day, with the daily dosage regimen being preferably from about 1 mg. to about 12 mg. When the method is carried out as described above, antiarthritic activity is produced.

One skilled in the art will recognize that in determining the amounts of the active ingredient in the claimed compositions and used in the claimed methods, the activity of the chemical ingredient as well as the size of the host animal must be considered.

The following examples are not limiting but are illustrative of the invention.

EXAMPLE 1

A solution of 14 g. of thiodiglycol in 35 ml. of ethanol was added to a solution of 22.1 g. of gold acid chloride trihydrate in 105 ml. of distilled water at 0° C. A solution of 10 g. of (diethyl)(phenyl)phosphine in 35 ml. of ethanol was then added dropwise. After stirring for 30 minutes, the mixture was extracted with chloroform and the chloroform extracts dried, filtered and the solvent removed in vacuo to give an oil. Purification of this oil by dry column chromatography and recrystallization from ether gave chloro[(diethyl) (phenyl)phosphine]gold(I) as white crystalline material having a melting point of 61°-63° C.

A cold solution of 1.66 g. (0.012 mole) of potassium carbonate in 20 ml. of distilled water was added to a solution of 5.3 g. (0.011 mole) of S-(2,3,4,6-tetra-O-acetyl-β-D-glucopyranosyl)thiopseudourea hydrobromide in 30 ml. of water at 0° C. A solution of 4.3 g. (0.01 mole) of chloro[(diethyl) (phenyl)phosphine]gold(I) in 60 ml. of ethanol containing 5 ml. of methylene chloride was then added and the mixture was stirred for three hours. The mixture was poured into 300 ml. of water and extracted with chloroform. The combined chloroform extracts were dried over magnesium sulfate, filtered and the solvent removed at reduced pressure to give S-[(diethyl) (phenyl)phosphine]gold(I) 2,3,4,6-tetra-O-acetyl-1-thio-β-D-glucopyranoside. Dry column chromatography (silica gel/ethyl acetate) gave purified product having $[\alpha]_D^{25°} = -61.6°$.

EXAMPLE 2

A solution of 13.4 g. (0.11 mole) of thiodiglycol in 30 ml. of ethanol was mixed with a solution of 20.0 g. (0.05 mole) of gold acid chloride trihydrate in 90 ml. of distilled water. When the solution was almost colorless, it was cooled to 0° C. and 10 g. (0.05 mole) of (diethoxy)(phenyl)phosphine in 30 ml. of ethanol was added dropwise to the stirred solution. After stirring for one hour, the two phase reaction mixture was extracted with chloroform and the combined chloroform extract was washed with water, dried over magnesium sulfate, filtered and the solvent removed from the filtrate at reduced pressure to give an oil. Chromatography ('Florisil'/chloroform) gave chloro[(diethoxy) (phenyl)phosphine]gold(I) as a colorless oil in the first fraction.

A cold solution of 2.5 g. (0.006 mole) of potassium carbonate in 20 ml. of distilled water was added to a solution of 2.8 g. (0.006 mole) of S-(2,3,4,6-tetra-O-acetyl-β-D-glucopyranosyl)thiopseudourea hydrobromide in 20 ml. of distilled water. After stirring for 15 minutes, a solution of 2.5 g. (0.005 mole) of chloro[(diethoxy)(phenyl)phosphine]gold(I) in 10 ml. of ethanol was added and the mixture was stirred at 0° C. for 90 minutes. The reaction mixture was then extracted with chloroform and the combined chloroform extracts were dried over magnesium sulfate, filtered and the solvent removed at reduced pressure to give, as the residue, S-[(diethoxy)(phenyl)phosphine]gold(I) 2,3,4,6-tetra-O-acetyl-1-thio-β-D-glucopyranoside. Dry column chromatography (silica gel/chloroform) gave purified product having $[\alpha]_D^{25°} = -57.7°$.

EXAMPLE 3

Using in place of (diethyl)(phenyl)phosphine in the procedure of Example 1, the following phosphines:

(dimethyl)(phenyl)phosphine
(dipropyl)(phenyl)phosphine
(dibutyl)(phenyl)phosphine
(di-isobutyl)(phenyl)phosphine
(ethyl)(methyl)(phenyl)phosphine
(methyl)(propyl)(phenyl)phosphine
(t-butyl)(methyl)(phenyl)phosphine the following products are obtained, respectively:

S-[(dimethyl)(phenyl)phosphine]gold(I) 2,3,4,6-tetra-O-acetyl-1-thio-β-D-glucopyranoside
S-[(dipropyl)(phenyl)phosphine]gold(I) 2,3,4,6-tetra-O-acetyl-1-thio-β-D-glucopyranoside
S-[(dibutyl)(phenyl)phosphine]gold (I) 2,3,4,6-tetra-O-acetyl-1-thio-β-D-glucopyranoside
S-[(di-isobutyl)(phenyl)phosphine]gold(I) 2,3,4,6-tetra-O-acetyl-1-thio-β-D-glucopyranoside
S-[(ethyl)(methyl)(phenyl)phosphine]gold(I) 2,3,4,6-tetra-O-acetyl-1-thio-β-D-glucopyranoside
S-[(methyl)(propyl)(phenyl)phosphine]gold(I) 2,3,4,6-tetra-O-acetyl-1-thio-β-D-glucopyranoside
S-[(t-butyl)(methyl)(phenyl)phosphine]gold(I) 2,3,4,6-tetra-O-acetyl-1-thio-β-D-glucopyranoside.

EXAMPLE 4

Using (dimethoxy)(phenyl)phosphine in place of (diethoxy)(phenyl)phosphine in the procedure of Example 2 gives, as the product, S-[(dimethoxy)(phenyl)phosphine]gold(I) 2,3,4,6-tetra-O-acetyl-1-thio-β-D-glucopyranoside.

Similarly, using (p-chlorophenyl)(diethoxy)phosphine and (p-bromophenyl)(diethoxy)phosphine, the corresponding S-[(p-chlorophenyl)(diethoxy)phosphine]gold(I) and S-[(p-bromophenyl)(diethoxy)phosphine]gold(I) 2,3,4,6-tetra-O-acetyl-1-thio-β-D- glucopyranosides are prepared. Also, using (diethoxy)(p-methoxyphenyl)phosphine in the procedure of Example 2, the product is S-[(diethoxy)(p-methoxyphenyl)phosphine]gold(I) 2,3,4,6-tetra-O-acetyl-1-thio-β-D-glucopyranoside.

In the same manner, using (phenyl)(dipropoxy)phosphine and (dibutoxy)(phenyl)phosphine, the products are S-[(phenyl)(dipropoxy)phosphine]gold(I) 2,3,4,6-tetra-O-acetyl-1-thio-β-D-glucopyranoside and the corresponding (dibutoxy)(phenyl)phosphine compound.

EXAMPLE 5

A solution of 10 g. (0.08 mole) of diethylphosphinous chloride in 100 ml. of ether was added to a solution of p-chlorophenyllithium [prepared from 15.4 g. (0.08 mole) of p-chlorobromobenzene in 100 ml. of ether and 54 ml. of 1.5M n-butyllithium in hexane] under a nitrogen atmosphere. After 30 minutes, the reaction mixture was quenched with a few drops of ethyl acetate and the solvent was removed at reduced pressure. Distillation of the residual oil gave (p-chlorophenyl)(diethyl)phosphine, b.p. 86°–89° C. at 1.5 mm.

A solution of 4.7 g. (0.038 mole) of thiodiglycol in 30 ml. of ethanol was added to a solution of 7.7 g. (0.019 mole) of gold acid chloride trihydrate in 45 ml. of distilled water. The colorless solution was cooled to 0° C. and a solution of 3.9 g. (0.019 mole) of (p-chlorophenyl)(diethyl)phosphine in 15 ml. of ethanol was added. After stirring for 45 minutes, the layers were separated and methylene chloride was added to the organic phase. The resulting solution was washed with distilled water, then dried with sodium sulfate, filtered and the solvent removed in vacuo to give an oily residue. This material was dissolved in ether and an equal volume of low boiling petroleum ether was added. The solid precipitate was filtered off and air dried to give chloro[(p-chlorophenyl)(diethyl)phosphine]gold(I), m.p. 77°–79° C.

Treating S-(2,3,4,6-tetra-O-acetylglucopyranosyl)thiopseudourea hydrobromide with aqueous potassium carbonate at 0°, then adding chloro[(p-chlorophenyl)-(diethyl)phosphine]gold(I) in ethanol containing a small amount of methylene chloride, stirring the resulting mixture for three hours and working up as in Example 1 gives S-[(p-chlorophenyl)(diethyl)phosphine]gold(I) 2,3,4,6-tetra-O-acetyl-1-β-D-glucopyranoside.

EXAMPLE 6

A solution of 10 g. (0.08 mole) of diethylphosphinous chloride in 100 ml. of ether was added to a solution of p-methoxyphenyllithium [prepared from 23.4 g. (0.1 mole) of p-iodoanisole in 100 ml. of ether and 62.5 ml. of 1.6 M n-butyllithium in hexane] under a nitrogen atmosphere. After 40 minutes, the reaction mixture was filtered and the solvent removed at reduced pressure. Distillation of the residual oil gave (diethyl)(p-methoxyphenyl)phosphine as a colorless liquid, b.p. 85°–90° C. at 0.5 mm.

A solution of 6.8 g. of thiodiglycol in 40 ml. of ethanol was added to a solution of 11.1 g. of gold acid chloride trihydrate in 60 ml. of distilled water. When the solution became colorless, it was cooled to 0° C. and a solution of 5.5 g. of (diethyl)(p-methoxyphenyl)phosphine in 15 ml. of ethanol was added. After stirring 20 minutes, the reaction mixture was extracted with methylene chloride. The combined methylene chloride extracts were washed with water, dried with sodium sulfate and the solvent removed at reduced pressure to give a pale gold oil. Purification was accomplished with dry column chromatography (alumina/chloroform) to give chloro[(diethyl)(p-methoxyphenyl)phosphine]gold(I) as a colorless oil.

Treating S-(2,3,4,6-tetra-O-acetyl-β-D-glucopyranosyl)thiopseudourea hydrobromide with aqueous potassium carbonate at 0° C., then adding chloro[(diethyl)(p-methoxyphenyl)phosphine]gold(I) in ethanol containing a small amount of methylene chloride, stirring the resulting mixture for three hours and working up as in Example 1 gives S-[(diethyl)(p-methoxyphenyl)phosphine]gold(I) 2,3,4,6-tetra-O-acetyl-1-thio-β-D-glucopyranoside.

EXAMPLE 7

Using the following tri-substituted phosphines in place of (diethoxy)(phenyl)phosphine in the procedure of Example 2:

(ethoxy)(methyl)(phenyl)phosphine
(ethoxy)(ethyl)(phenyl)phosphine
(butoxy)(ethoxy)(phenyl)phosphine
(p-chlorophenyl)(ethoxy)(ethyl)phosphine the following products are obtained, respectively:

S-[(ethoxy)(methyl)(phenyl)phosphine]gold(I) 2,3,4,6-tetra-O-acetyl-1-thio-β-D-glucopyranoside
S-[(ethoxy)(ethyl)(phenyl)phosphine]gold(I) 2,3,4,6-tetra-O-acetyl-1-thio-β-D-glucopyranoside
S-[(butoxy)(ethoxy)(phenyl)phosphine]gold(I) 2,3,4,6-tetra-O-acetyl-1-thio-β-D-glucopyranoside
S-[(p-chlorophenyl)(ethoxy)(ethyl)phosphine]gold(I) 2,3,4,6-tetra-O-acetyl-1-thio-β-D-glucopyranoside.

By the same procedure, using (2-chlorophenyl)(diethyl)phosphine, the product is S-[(2-chlorophenyl)(diethyl)phosphine]gold(I) 2,3,4,6-tetra-O-acetyl-1-thio-β-D-glucopyranoside.

EXAMPLE 8

Using, in the procedure of Example 1, (4-bromophenyl)(diethyl)phosphine in place of (diethyl)(phenyl)phosphine, the product is S-[(4-bromophenyl)(diethyl)phosphine]gold(I) 2,3,4,6-tetra-O-acetyl-1-thio-β-D-glucopyranoside.

Similarly, using (4-ethoxyphenyl)(diethyl)phosphine, the product is S-[(4-ethoxyphenyl)(diethyl)phosphine]gold(I) 2,3,4,6-tetra-O-acetyl-1-thio-β-D-glucopyranoside.

EXAMPLE 9

Chloro[(diethyl)(phenyl)phosphine]gold(I) (3.98 g., 0.01 mole) in 50 ml. of ethanol is added to a cold, stirred solution of 2.54 g. (0.01 mole) of sodium 1-thio-β-D-glucopyranose dihydrate in distilled water. The mixture is stirred for three hours, then poured into water and extracted with chloroform. The chloroform extracts are dried and filtered and the solvent is removed in vacuo to give S-[(diethyl)(phenyl)phosphine]gold(I) 1-thio-β-D-glucopyranoside.

In the same manner, other S-(tri-substituted phosphine)gold(I) 1-thio-β-D-glucopyranosides may be prepared using the chloro(tri-substituted phosphine)gold(I) compounds prepared as described herein.

EXAMPLE 10

S-[(Diethyl)(phenyl)phosphine]gold(I) 1-thio-β-D-glucopyranoside (5.5 g.) is dissolved in 100 ml. of methyl isocyanate and the mixture is stirred at room temperature for 4 hours. The solution is evaporated at reduced pressure and the residue was chromatographed on silica with chloroform and methanol to give S-[(diethyl)(phenyl)phosphine]gold(I) 2,3,4,6-tetra-O-(N-methylcarbamoyl)-1-thio-β-D-glucopyranoside.

Similarly, using ethyl isocyanate and butyl isocyanate in the above procedure, the following are prepared:

S-[(diethyl)(phenyl)phosphine]gold(I) 2,3,4,6-tetra-O-(N-ethylcarbamoyl)-1-thio-β-D-glucopyranoside
S-[(diethyl)(phenyl)phosphine]gold(I) 2,3,4,6-tetra-O-(N-butylcarbamoyl)-1-thio-β-D-glucopyranoside.

In the same manner, other S-(tri-substituted phosphine)gold(I) 2,3,4,6-tetra-O-(N-lower alkycarbamoyl)-1-thio-β-D-glucopyranosides may be prepared using other S-(tri-substituted phosphine)gold(I) 1-thio-β-D-glucopyranosides prepared as described in Example 9.

EXAMPLE 11

2,3,4,6-Tetra-O-acetyl-1-thio-β-D-glucopyranose, obtained from the hydrolysis of 29 g. of S-(2,3,4,6-tetra-O-acetyl-β-D-glucopyranosyl)thiopseudourea hydrobromide as in "Methods in Carbohydrate Chemistry", Vol. II, page 436 (Whistler and Wolfrom editors, Academic Press Inc., 1963) was dissolved in 250 ml. of chloroform and cooled to 0°–5° C. in an ice bath. Anhydrous pyridine (20 ml.) was added, followed by 27.9 g. of trityl chloride. The mixture was stirred overnight at ambient temperature and the organic solution was extracted with dilute hydrochloric acid, washed with 5% aqueous sodium carbonate solution and with brine, dried over magnesium sulfate and evaporated under reduced pressure. The residue was crystallized from ether, then recrystallized from benzene-cyclohexane to give S-trityl-2,3,4,6-tetra-O-acetyl-1-thio-β-D-glucopyranose, m.p. 177.5°–179.5° C.

S-Trityl-2,3,4,6-tetra-O-acetyl-1-thio-β-D-glucopyranose (21.0 g.) was suspended in 90 ml. of methanol, cooled to −15° C. and a solution of sodium methoxide prepared from 0.21 g. of sodium and 75 ml. of methanol was added. The mixture was stirred for one hour at room temperature, then concentrated under reduced pressure to give a solid residue. The residue was triturated with water, then chloroform was added. The mixture was filtered and concentrated to give a solid residue which was dried by azeotropic distillation in benzene. Further evaporation of solvent and drying in vacuo gave S-trityl-1-thio-β-D-glucopyranose.

S-Trityl-1-thio-β-D-glucopyranose (3.6 g.) was dissolved in 50 ml. dry pyridine, cooled to 0° while 5 ml. (7.5 g.) of methylsulfonyl chloride was added. The solution was placed in the refrigerator for 22 hours until thin layer chromatography showed only traces of starting material or partially reacted products remaining. The solvent was removed at reduced pressure. The oily residue was dissolved in chloroform (200 ml.) and was washed with dilute hydrochloric acid and brine. Evaporating the dried organic extract yielded a product which was chromatographed over a silica dry-column using 20% ethyl acetate-80% chloroform eluant. Pure S-trityl-2,3,4,6-tetra-O-methylsulfonyl-1-thio-β-D-glucopyranose was obtained from ether.

S-Trityl-2,3,4,6-tetra-O-methylsulfonyl-1-thio-β-D-glucopyranose (1.8 g.) was dissolved in 6 ml. of methylene chloride and 12 ml. methanol and 0.41 g. of granular silver nitrate was added. The mixture was allowed to stand overnight at room temperature yielding a solid precipitate, the silver salt of 2,3,4,6-tetra-O-methylsulfonyl-1-thio-β-D-glucopyranose, which was filtered and dried.

The silver salt (2.0 g.) prepared above is dissolved in 200 ml. of tetrahydrofuran and 1.3 g. of chloro[(diethyl)(phenyl)phosphine]gold(I) is added. The progress of the reaction is monitored with thin layer chromatography and after completion (5–7 hours), the silver chloride precipitate is filtered and the solution is evaporated at reduced pressure to give S-[(diethyl)(phenyl)phosphine]gold(I) 2,3,4,6-tetra-O-methylsulfonyl-1-thio-β-D-glucopyranoside.

Substituting an equivalent amount of ethylsulfonyl chloride in place of the methylsulfonyl chloride in the above procedure gives S-[(diethyl)(phenyl)phosphine]gold(I) 2,3,4,6-tetra-O-ethylsulfonyl-1-thio-β-D-glucopyranoside. Substituting an equivalent amount of isopropylsulfonyl chloride gives the corresponding tetra-O-isopropylsulfonyl compound.

EXAMPLE 12

1-Bromo-2,3,4,6-tetra-O-methyl-β-D-glucopyranose (10 g.), prepared according to the method of Levene et al. [*J. Biol. Chem.*: 98, 17 (1932)], was dissolved in 50 ml. of acetone and 2.90 g. of thiourea was added. The displacement reaction was allowed to proceed under reflux until the presence of the bromoglucose starting material was no longer detected by thin layer chromatography (2–2.5 hours). The solution was cooled, the solvent was removed under reduced pressure, and the resultant oil was taken up in 50 ml. of water and heated to 85°–90° C. on the steam bath. Sodium bisulfite (10 g.) was added in one portion, the temperature of the mixture was maintained for 5 minutes with constant swirling and heating was discontinued. The solution was allowed to cool to room temperature, it was saturated with sodium sulfate and extracted with chloroform. The oily 1-thio-2,3,4,6-tetra-O-methyl-β-D-glucopyranose obtained by evaporation of the dried organic extracts was used directly in the next step.

1-Thio-2,3,4,6-tetra-O-methyl-β-D-glucopyranose (1.66 g.) is dissolved in 18 ml. of water and a solution of 1.0 g. of potassium carbonate in 12 ml. of water is added. The mixture is cooled to −15° C. and 2.7 g. of chloro[(diethyl)(phenyl)phosphine]gold(I) is added in 18 ml. of ethanol. Cooling and stirring are maintained for 1.5 hours. The mixture is allowed to come to ambient temperature. The solution is concentrated at reduced pressure then partitioned between water and methylene chloride. The organic extract is dried over magnesium sulfate, filtered and concentrated. The resulting residue is chromatographed by dry-column chromatography over silica gel using ethyl acetate as eluant to give S-[(diethyl)(phenyl)phosphine]gold(I) 2,3,4,6-tetra-O-methyl-1-thio-β-D-glucopyranoside.

EXAMPLE 13

| Ingredients | Amounts |
| --- | --- |
| S-(diethyl)(phenyl)phosphinegold(I) 2,3,4,6-tetra-O-acetyl-1-thio-β-D-glucopyranoside | 5 mg. |
| magnesium stearate | 5 mg. |

| Ingredients | Amounts |
| --- | --- |
| lactose | 150 mg. |

The above ingredients are screened, mixed and filled into a hard gelatin capsule.

The capsules are administered orally to a subject in need of antiarthritic treatment in amounts within the daily dose range given hereabove.

Similarly, the other gold compounds of Formula I may be formulated into capsules by the procedure of Example 13.

Other pharmaceutical compositions such as tablets containing a compound of Formula I as the active ingredient are formulated by standard procedures.

What is claimed is:

1. A compound of the formula:

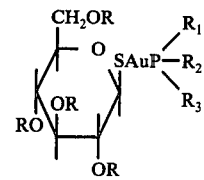

in which:
R is hydrogen, acetyl, lower alkyl-NHCO, lower alkyl-SO$_2$ or lower alkyl;
R$_1$ is phenyl optionally substituted by halogen or lower alkoxy and
R$_2$ and R$_3$ are lower alkyl or lower alkoxy.

2. A compound of claim 1 in which R is acetyl.

3. A compound of claim 1 in which R$_2$ and R$_3$ are ethyl.

4. A compound of claim 1, said compound being S-[(diethyl)(phenyl)phosphine]gold(I) 2,3,4,6-tetra-O-acetyl-1-thio-β-D-glucopyranoside.

5. A compound of claim 1, said compound being S-[(diethyl)(phenyl)phosphine]gold(I) 2,3,4,6-tetra-O-acetyl-1-thio-β-D-glucopyranoside.

6. A pharmaceutical composition having antiarthritic activity, in dosage unit form, comprising a pharmaceutical carrier and a compound of claim 1.

7. A method of producing antiarthritic activity which comprises administering internally to an animal a compound of claim 1.

* * * * *